(12) United States Patent
Kurth et al.

(10) Patent No.: US 8,461,587 B2
(45) Date of Patent: Jun. 11, 2013

(54) ION-SENSITIVE SENSOR WITH MULTILAYER CONSTRUCTION IN THE SENSITIVE REGION

(75) Inventors: Eberhard Kurth, Moritzburg (DE); Christian Kunath, Dresden (DE); Torsten Pechstein, Radebeul (DE)

(73) Assignee: Endress + Hauser Conducta Gesellschaft für Mess- und Regeltechnik mbH + Co. KG, Gerlingen (DE)

( * ) Notice: Subject to any disclaimer, the term of this patent is extended or adjusted under 35 U.S.C. 154(b) by 12 days.

(21) Appl. No.: 13/260,739

(22) PCT Filed: Mar. 15, 2010

(86) PCT No.: PCT/EP2010/053275
§ 371 (c)(1),
(2), (4) Date: Sep. 28, 2011

(87) PCT Pub. No.: WO2010/112324
PCT Pub. Date: Oct. 7, 2010

(65) Prior Publication Data
US 2012/0018722 A1  Jan. 26, 2012

(30) Foreign Application Priority Data
Mar. 31, 2009 (DE) .......... 10 2009 002 060

(51) Int. Cl.
*H01L 29/66* (2006.01)
*H01L 21/02* (2006.01)

(52) U.S. Cl.
USPC .......... 257/43; 257/E21.002; 257/E29.166; 257/253; 438/49

(58) Field of Classification Search
USPC ............ 257/43, E21.002, E29.166, 253
See application file for complete search history.

(56) References Cited

U.S. PATENT DOCUMENTS 4,180,771 A * 12/1979 Guckel ............ 324/71.1
4,636,827 A * 1/1987 Rudolf ............ 257/253

(Continued)

FOREIGN PATENT DOCUMENTS

DE 42 32 532 4/1994
KR 10-2008-0098913 11/2008

(Continued)

OTHER PUBLICATIONS

Yi Liu, Tianhong Cui; Ion-sensitive field-effect transistor based pH sensors using nano self-assembled polyelectrolyte/nanoparticle multilayer films; Jun. 22, 2006; ScienceDirect.*
German Search Report in corresponding German Application No. 10 2009 002 060.8.
International Search Report in corresponding International Application PCT/EP2010/053275 dated Jun. 30, 2010.

(Continued)

*Primary Examiner* — Marcos D. Pizarro
*Assistant Examiner* — Hoan Nguyen
(74) *Attorney, Agent, or Firm* — Bacon & Thomas, PLLC

(57) ABSTRACT

An ion-sensitive sensor with an EIS structure includes: a semiconductor substrate, on which a layer of a substrate oxide 103 is produced; an adapting or matching layer, which is prepared on the substrate oxide; a chemically stable intermediate insulator, which is deposited on the adapting or matching layer; and a sensor layer, which comprises a tantalum oxide or a tantalum oxynitride, and which is applied on the intermediate insulator; wherein the intermediate insulator comprises hafnium oxide or zirconium oxide or a mixture of zirconium oxide and hafnium oxide, and wherein the adapting or matching layer differs in its chemical composition and/or in its structure from the intermediate insulator and from the substrate oxide.

9 Claims, 1 Drawing Sheet

U.S. PATENT DOCUMENTS

| | | | |
|---|---|---|---|
| 5,182,005 A * | 1/1993 | Schwiegk et al. | 204/435 |
| 6,617,190 B2 * | 9/2003 | Chou et al. | 438/49 |
| 7,103,484 B1 | 9/2006 | Shi et al. | |
| 7,355,200 B2 * | 4/2008 | Kurth et al. | 257/48 |
| 2002/0109261 A1 * | 8/2002 | Grosz et al. | 264/255 |
| 2004/0079636 A1 * | 4/2004 | Hsia et al. | 204/403.01 |
| 2005/0156584 A1 * | 7/2005 | Feng | 324/71.5 |
| 2006/0060924 A1 * | 3/2006 | Ogawa et al. | 257/364 |
| 2009/0014757 A1 * | 1/2009 | Takulapalli et al. | 257/253 |
| 2010/0126885 A1 * | 5/2010 | Iechi et al. | 205/793 |
| 2010/0301398 A1 * | 12/2010 | Rothberg et al. | 257/253 |
| 2012/0055236 A1 * | 3/2012 | Takulapalli | 73/31.06 |

FOREIGN PATENT DOCUMENTS

| | | |
|---|---|---|
| WO | WO 2004/079355 | 9/2004 |
| WO | WO 2005/073706 | 8/2005 |

OTHER PUBLICATIONS

H. Gruger et al., "High quality r.f. sputtered metal oxides (Ta2O5, HfO2) and their properties after annealing", Thin Solid Films, Bd. 447-448, Jan. 30, 2004, pp. 509-515.

P.V. Bobrov et al., "Chemical sensitivity of an ISFET with Ta2O5 membrane in strong acid and alkaline solutions", Sensors and Actuators B, vol. 3, No. 1, Jan. 1, 1991, pp. 75-81.

T. Mikolajick et al., "The pH-sensing properties of tantalum pentoxide films fabricated by metal organic low pressure chemical vapor deposition", Sensors and Actuators B, vol. 44, Nos. 1-3, Oct. 1, 1997, pp. 262-267.

English Translation of International Report on Patentability in corresponding International Application PCT/EP2010/053275.

* cited by examiner

ION-SENSITIVE SENSOR WITH MULTILAYER CONSTRUCTION IN THE SENSITIVE REGION

TECHNICAL FIELD

The present invention relates to an ion-sensitive sensor having an electrolyte insulator semiconductor structure (EIS), especially an ion-sensitive field effect transistor (IS-FET) or an ion-sensitive sensor having an EIS structure and light supported measured value registering.

BACKGROUND DISCUSSION

A sensor having an EIS structure includes a semiconductor substrate on which an insulator is arranged, which is supplied with an electrolyte in measurement operation.

ISFETs are established examples of sensors having an EIS structure, wherein, in this case, the insulator forms the ion-sensitive gate insulator of a field effect transistor.

In the case of the so-called LAPS (light addressable potentiometric sensors), by means of a modulated light signal, photoelectrons are produced in the semiconductor material— an EIS structure—wherein the generating of photoelectrons, in turn, depends on the electrolyte properties. A basic description of LAPS is given by Hafeman et al. in "Light Addressable Potentiometric Sensor for Biochemical Systems", Science 240 (1988) 1182-1185.

ISFETs are established and better investigated than other EIS structures. Therefore, in the following description of problems in the state of the art, reference is essentially made to ISFETs, in which case it is understood that these problems exist correspondingly for other sensors with an EIS structure.

Ion-sensitive field effect transistors ISFET) are applied for measuring ion concentrations or special substance concentrations in solutions of various compositions and conductivities. Applications of ISFETs for continuous detection of concentrations are to be found in environmental monitoring, in industrial process monitoring, in the foods industry and in biochemistry/medical technology. In such cases, a highly precise registration of concentration, fast start-up and minimal long-term drift of the sensor are especially of importance, coupled with an acceptable price.

LITERATURE

/1/ "Chemical sensitivity of an ISFET with $Ta_2O_5$ membrane in strong acid and alkaline solutions", P.V.Bobrov, etal., Leningrad State University USSR, Sensor and Actuators B 3 (1991) 75-81

/2/ "The pH-sensing properties of tantalum pentoxide films fabricated by metal organic low pressure chemical vapor deposition", T.Mikolajick, eta)., Fraunhofer Institute Integrated Circuits Erlangen Germany, Sensors and Actuators B 44 (1997) 262-267

/3/ Sensitivity and hysteresis effect in $Al_2O_3$ gate pH ISFET, Jung-Chuan Chou et.al., National Yunlin University Taiwan, Materials Chemistry and Physics 71 (2001) 120-4

/4/ "Study of $TiO_2$ thin films for Ion Sensitive Field Effect Transistor Application with RF sputtering deposition", Jung Chuan Chou, Lan Pin Liao, National Yunlin University of Science & Technology, Taiwan, Japanese Journal of Applied Physics 43, 1,2004 pp.61-65

/5/ "Development of a wide range pH sensor based on Electrolyte-Insulator-Semiconductor structure with corrosion-resistant $Al_2O_3$-$Ta_2O_5$ and $Al_2O_3$-$ZrO_2$ double-oxide thin films", Shoji Yoshida, et. al., Tohoku University Sendai Japan, J.Electrochem.Soc.151(3)Pg. 53-Pg. 58 (2004)

/6/ "pH sensitivity improvement on 8nm thick hafnium oxide by post deposition annealing", Chao-Sung Lai et.al., Chang Gung University Tao-Yuan Taiwan, Electrochemical and Solid-State Letters 9(3) Pgs. 90-2(2006)

/7/ J.G.Vlasov et.al., Journal Prikladnoi Chimi 61 (1988) 767-771

/8/ Dorota Sobczynska et.al., Sensors and Actuators 6 (1984) 93-105

/9/ U.S. Pat. No. 5,288,563

/10/ International Patent WO2005/073706

/11/ H.Remy, Lehrbuch der anorganischen Chemie, Volume 1, 13th Edition, Akademische Verlagsgesellschaft Geest&Portig K.-G., Leipzig 1970

/12/ Jung-Chuan Chou, Chen-Yu Weng, Materials Chemistry and Physics 71 (2001) 120-124

/13/ Chao-Sung Lai et.al., Electrochemical and Solid-State Letters 9(3) Pgs. 90-2 (2006)

/14/ Helmut Galster, "pH-Messung ", VCH Weinheim 1990, Pg.108

/15/ M.Balog et.al., Thin Solid Films 41(1977)247-59

/16/ P.R. Chalker, et.al. Appl. Phys. Letters 93, 182911 (2008)

/17/ Yim Fun Loo et. A1., J. Appl. Phys. 99, 103704 (2006)

The sensitive layers of ion-sensitive field effect transistors are almost exclusively amorphous layers of simple metal oxides, such as, for example, $Ta_2O_5$ /1,2/, $Al_2O_3$ /3/, $TiO_2$ /4/, $HfO_2$ /6/, and simple metal nitrides /9/, or double metal oxide mixtures, such as, for example, TaAlO and ZrAlO /5/, or combinations of two different amorphous metal oxide layers /10/, which always lie on $SiO_2$.

In semiconductor technology and also in sensor manufacturing technology, the structures of simple metal oxide layers or silicon nitride layers or simple metal oxynitride layers are most typically optimized toward being a layer which is as amorphous as possible /13/. In the presence of very high temperatures and ion concentrations, simple crystalline metal oxide layers are penetrated and underetched on the grain boundaries, so that these layers are dissolved away in parts, and finally are completely destroyed. If the ions of the measured solution penetrate into the semiconductor Si or into its oxide layer, the sensor becomes unusable /10/.

Other reasons for the amorphous layers are that they give as linear pH sensor properties as possible, and also response times which are as short as possible. In /6,7/, amorphous $HfO_2$ shows a markedly better pH linearity than does polycrystalline $HfO_2$ /7,8/.

Other areas of semiconductor manufacture, for instance for integrated circuits, develop their process parameters in such a manner that amorphous layers arise as gate insulators, for instance to minimize leakage current through the layers. On the other hand, the etch rate of amorphous layers in hydrofluoric acid is much greater than that of annealed crystalline metal oxide layers /15/.

In the processes industry, ISFET sensors are often subjected to strenuous cleaning procedures, so-called "Cleaning In Process", or CIP. In /10/, $Al_2O_3$ is utilized as a first metal oxide layer and $Ta_2O_5$ as a cover layer. It is described in this patent that the $Ta_2O_5$ layer is partially etched through in hot alkaline solutions during the CIP, and the sensor thus becomes unusable. As a result, an aluminum oxide layer was arranged under the $Ta_2O_5$ on the substrate oxide $SiO_2$. It is assumed that, via the known high chemical stability of aluminum oxide against alkaline solutions, the aluminum oxide can be utilized as a barrier layer against the penetration of the alkaline solutions into the $SiO_2$. In this arrangement, the advantages of the individual layers of aluminum oxide and $Ta_2O_5$ are combined, namely the very good pH sensor properties and excellent acid resistance of the $Ta_2O_5$ with the more alkaline solution resistant aluminum oxide.

The properties of aluminum oxide are, however, many and strongly dependent on the manufacturing technology. Aluminum oxide occurs in a large number of crystallographic and other structural modifications, which all can be stable in the case of working temperatures of the pH measuring, wherein, however, not all necessarily have the desired chemical stability against alkaline solutions. Tn order to obtain the modification for alkaline solution stability, the layer must be heated up to at least 1000° C., in order to allow the layer to crystallize into the alpha-form of $Al_2O_3$. In all conventional layer deposition technologies of semiconductor processes, $Al_2O_3$ occurs in amorphous form. If amorphous $Al_2O_3$ comes in contact with aqueous media, the metal oxide is hydrated, which further increases the number of possible modifications /11/. This morphological multiplicity leads to strong layer stress changes, when the layer is heated to 1000° C. When the $Al_2O_3$ is to be applied in a crystalline phase for the purpose of alkaline solution stability, additionally, a thicker layer is required, since attack of the alkaline solution through the grain boundaries can otherwise lead to the occurrence of leakage currents.

If the $Al_2O_3$ is not sufficiently cured, drift and light sensitivity of the sensor moreover increase /12/.

Although $Al_2O_3$ improves the alkaline solution stability, it can nevertheless degrade the sensor accuracy, for it has a relatively low dielectric constant of 9 to 10. With a low dielectric constant, only low transistor slopes can be achieved. Thus, sensor accuracy increases with transistor slope.

$Ta_2O_5$ is the anhydride of tantalic acid, therefore $Ta_2O_5$ above pH10 is unstable at high temperatures; below pH10, however, it displays, as is known, the best pH linearity and acid stability, the lowest drift, as well as the smallest hysteresis of all metal oxides. On the other hand, tantalic acid thermodynamically has a still lower solubility in alkaline solutions than aluminum oxide and aluminum hydroxide compounds, since aluminum has an amphoteric character and can form aluminates. The stability of the alpha-$Al_2O_3$ against alkaline solutions is solely determined by the lattice structure of the solid body.

Besides CIP, the process industry also uses SIP (sterilization in process). In such case, hot steam of more than 130° C. is supplied to the sensors. When sensors are electrically operated under these extreme conditions, they experience a loading, which, in the case of sensors according to the state of the art, can lead to premature failure, either due to electrical drift of the sensor working point or due to electrochemical destruction.

SUMMARY OF THE INVENTION

In view of the problems described above, an object of the present invention is to provide a media-resistant, ion-sensitive sensor having an EIS structure, for example, an ISFET sensor or an ion-sensitive LAPS, coupled with a sufficiently high sensitivity.

For achieving the object, metal oxides of the transition elements as well as the rare earth metals with higher dielectric constants are especially suitable. Therewith, greater layer thicknesses are possible, which are used, in order to keep the sensor functionally capable in strongly corroding media for as long as possible.

The ion-sensitive sensor of the invention with an EIS structure includes a semiconductor substrate, on which a layer of a substrate oxide is produced, an adapting or matching layer, which is prepared on the substrate oxide, a chemically stable intermediate insulator, which is deposited on the adapting or matching layer, and a sensor layer, which comprises a tantalum oxide or a tantalum oxynitride, and which is applied on the intermediate insulator, wherein the intermediate insulator comprises hafnium oxide or zirconium oxide or a mixture of these oxides, and wherein the adapting or matching layer differs in its chemical composition and/or in its structure from the intermediate insulator and from the substrate oxide.

The substrate oxide, the adapting or matching layer, the intermediate insulator and the sensor layer together form the insulator of the EIS structure.

In the measurement operation, the sensor layer of the insulator can be supplied with a measured medium, wherein the measured medium, due to its electrolyte properties, stands for the "E" in the "EIS" structure.

The sensor of the invention with EIS structure can comprise especially an ISFET sensor or pH ISFET sensor or a LAPS.

In a further development of the invention, the adapting or matching layer includes at least one material selected from the group of materials that includes: Hafnium oxide silicate, zirconium oxide silicate, mixtures of hafnium oxide-zirconium oxide silicate, hafnium oxynitride silicate, zirconium oxynitride silicate, mixtures of hafnium oxynitride zirconium oxynitride silicate, hafnium oxide, tantalum oxide, tantalum oxynitride, tantalum hafnium oxynitride mixtures of tantalum hafnium oxide silicate, mixtures of tantalum hafnium oxynitride silicate, hafnium lanthanum oxide, hafnium lanthanum oxynitride, hafnium cerium oxide or hafnium cerium oxynitride.

In a further development of the invention, the substrate oxide has a layer thickness of 2.5 nm to 150 nm, especially not less than 10 nm and not more than 90 nm.

In a further development of the invention, the layer thickness of the adapting or matching layer amounts to 1 nm to 135 nm, especially not less than 5 nm and not more than 40 nm.

According to a further development of the invention, the intermediate insulator has a layer thickness of 20 nm to 200 nm, especially not less than 30 nm and not more than 170 nm, preferably not less than 50 nm and not more than 150 nm.

According to a further development of the invention, the sensor layer has a layer thickness of 10 nm to 200 nm, especially not more than 100 nm, and preferably not more than 50 nm.

According to a further development of the invention, the substrate comprises silicon, especially n-silicon.

According to a further development of the invention, the sensor with EIS structure comprises an ISFET in the form of a p-channel field effect transistor, or an n-channel field effect transistor in a p-well.

According to a further development of the invention, the adapting or matching layer between the substrate oxide and the intermediate insulator comprises a transition from an amorphous to a nano-crystalline structure.

According to a further development of the invention, the intermediate insulator has a polycrystalline structure, especially a nano-crystalline structure.

According to a further development of the invention, the sensor layer has an amorphous, partially crystalline or polycrystalline structure, especially a nano-crystalline structure.

The method of the invention for manufacture of an ion-sensitive field effect transistor of the invention includes preparing the described layer sequence, wherein especially the intermediate insulator is deposited in a crystalline or high-density amorphous or partially crystalline form.

According to a further development of the invention, the intermediate insulator and sensor layer are together cured, and the crystallinity set, via an annealing.

According to a further development of the invention, the substrate oxide is increased in its thickness via a heat treatment, wherein, by means of a controlled annealing, the layer thickness can be controlled and sensor parameters dependent thereon set as desired.

According to a further development of the invention, the metal oxides, metal oxynitrides, metal oxide silicates, metal oxynitride silicates are applied via sputtering, electron beam evaporation or CVD deposition.

According to a further development of the invention, metals, metal nitrides, metal silicides, and metal nitride silicides are applied via sputtering, electron beam evaporation or via a CVD deposition and oxidized in a subsequent step.

According to a further development of the invention, the crystalline deposition occurs with high particle energies on unheated substrates.

According to another further development of the invention, the crystalline deposition occurs on substrates at more than 250° C., wherein, also in this case, the crystalline deposition can occur with high particle energies.

Advantages and aspects of the invention and its further developments are summarized as follows.

The requirement of high chemical stability precludes that the same layer material can undertake a pH sensory task with sufficient linearity and small hysteresis. At the same time, its pH sensitivity must be sufficiently good precisely under extreme pH values, so that in these corroding solutions at high temperatures, the sensor does not immediately become unsuitable, although holes or gaps are etched into the pH sensor layer and the hydrated surface zone grows.

A chemically stable layer must be a high density material, which is as self-contained as possible. A high density, chemically stable material, as a relatively thick layer, does not, however, have a very good adhesion on a substrate base such as the oxidized silicon wafer, when the wafers are exposed to different temperature loadings in the semiconductor process. The silicon wafer itself must be oxidized, so that the field effect transistor receives stable parameters. This substrate oxide $SiO_2$ serves simultaneously as a protective layer against metal ions which diffuse in from the layers lying thereover, and electrically insulates from the metal oxides, whose electrical insulation effect becomes smaller under SIP-conditions. Since the oxide of the silicon has a very small dielectric constant, its layer thickness is preferably kept small.

Since the sensor structure is exposed to electrochemical stress, the installed materials must be as redox stable as possible. The required combination of a plurality of layers should especially occur in such a manner that the grain boundaries of the metal compounds do not propagate in a manner traversing from the surface up to the $SiO_2$, to stress the $SiO_2$ or even crack it open.

High-density crystallinely deposited metal oxides (for example $HfO_2$) with high dielectric constants and sufficient pH sensitivity are characterized by a very high chemical resistance especially in strongly alkaline measured media even at high temperatures, whereby they are very well-suited as intermediate insulators under the pH linear sensor layer, and significantly lengthen the lifetime of the sensor. Materials with higher dielectric constants in any event display lower electrical leakage currents at equal effective insulation thicknesses. The stability of the crystalline deposited material is so high that a shared annealing with the layers lying thereabove and thereunder does not lead to mixing, and thereby, disturbances in the layers do not occur. Once deposited in crystalline form, the structure scarcely changes when the temperature of the layer is increased. A structural change would first occur in the case of the next phase transition, which, however, does not occur under the usual conditions.

BRIEF DESCRIPTION OF THE DRAWINGS

The invention will now be explained in greater detail on the basis of the appended drawing, the figures of which show as follows.

DETAILED DISCUSSION IN CONJUNCTION WITH THE DRAWINGS

Figure 1:
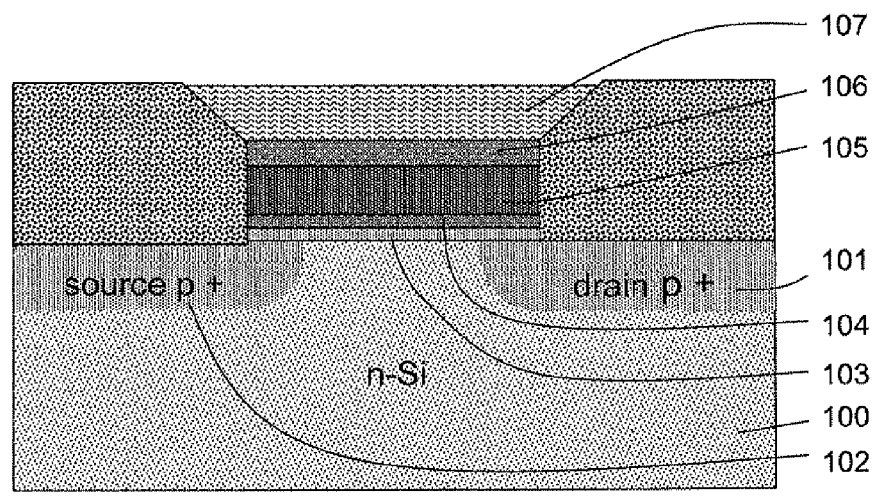
FIG. 1: is a schematic longitudinal section through a pH ISFET sensor of the invention.

In the illustrated sketch, a longitudinal section of an ISFET sensor chip of the invention is presented. The chip with an area of about 3.5×3.5 mm² is manufactured in composite on 150 mm silicon wafers in a semiconductor production line. Separated chips are adhered on suitable substrates, contacted, and, by means of special construction methods, are finished to form complete measuring systems. From the chips/boards, for example, immersion electrodes for measuring pH are produced.

The ISFET sensor of the invention has essentially the following structure. A substrate oxide 103 on a silicon substrate 100 forms the gate oxide and stabilizes the field effect, which is induced by a multilayer stack, composed of a sensor layer 106, intermediate insulator 105, adapting or matching layer 104 and substrate oxide 103, upon supply of a measured solution 107. The field effect enables a channel current between a source 102 and drain 101, when, between source 102 and drain 101, an electrical potential difference is set via an electrical contacting of source 102 and drain 101. The action of the field effect transistor can also be controlled via electrical contacting of the silicon bulk 100.

The adapting or matching layer 104 produced according to the invention which lies under the high-density intermediate insulator 105, improves the adhesion of the double layer stack of intermediate insulator 105/pH sensor layer 106, interrupts grain boundary propagation toward substrate 100, and therewith likewise lengthens the sensor lifetime of the sensor. Adapting or matching layer 104 also optimizes the mechanical stresses in the multilayer stack. Adapting or matching layer 104 structurally and electrically matches the otherwise abrupt structural transition from the $SiO_2$, which still remains amorphous even in the case of very high temperatures, to the crystalline metal oxide $HfO_2$ of the intermediate insulator 105.

All properties required for the chemically resistant and SIP-stable pH sensor are, as a result, obtained by producing a multilayer, especially a triple layer, on the substrate oxide, for example $SiO_2$.

The triple layer arises by insertion of the adapting layer between the substrate oxide 103 $SiO_2$ and the double-layer, intermediate insulator 105 and pH sensor layer 106. Substrate oxide 103 is 25 to 1500 Angstroms thick.

Adapting or matching layer 104 can be metal oxide silicate compounds, specially produced metal oxides or metal oxynitrides or metal oxynitride silicates, which, with their specific structure, serve as structure matching for the intermediate insulator 105. The adapting or matching layer 104 can only be crystallized with difficultly, even in the case of higher process temperatures, and can have a structure ranging from amorphous to crystalline. The adapting or matching layer 104 is preferably a specially structured $Ta_2O_5$ or an Hf or Zr silicate compound with a thickness of 10 to 1350 Angstroms.

The intermediate insulator 105, preferably $HfO_2$, is deposited in crystalline form during its manufacture. The happens either via CVD processes at substrate temperatures of more than 250° C., or via PVD processes with high particle energy, either at room temperature, or likewise in the case of substrate temperatures over 250° C., but occurs then, however, with somewhat lower particle energies. Instead of $HfO_2$, also $ZrO_2$, $TiO_2$, oxides of the $3^{rd}$ group of the periodic system and rare earth metal oxides or their mixtures can be used. The intermediate insulator 105 is preferably 200 to 2000 Angstroms thick.

Deposited on the crystalline intermediate insulator 105 is the sensor layer 106, preferably amorphous or partially crystalline $Ta_2O_5$ of 100 to 2000 Angstroms thickness, which, at high temperatures and by means of special gases and gas mixtures, is, together with the other layers and the substrate, crystallized, cured and firmly bonded with the intermediate insulator 105. In such case, the surface of the tantalum oxide enlarges, and the desired small hysteresis with high pH linearity is achieved.

Via annealing processes with oxidizing gases, the substrate oxide thickness 103 can be increased as desired by diffusion through the metal oxides. This substrate surface adjustment can occur via oven processes at temperatures greater than 750° C. over a longer period of time (>30 min), or can occur in a matter of seconds via RTA processes at temperatures of 1150° C. A combination of both processes is sensible or necessary for targeted curing near the surface coupled with simultaneous deep-penetrating oxidation.

According to the invention, the layers of the adapting or matching layer 104, intermediate insulator 105, and pH sensor layer 106 are deposited by sputtering the metals or the metal oxides by means of $Ar/O_2$, or by CVD, and produced and conditioned by annealing in oxidizing and reducing gases. The heat treatments range from 1000° C. to 400° C.

Via application of metal oxide components with high dielectric constants, which, at high temperatures, are porous or conductive for oxygen ions, the entire layered stack can, in a single step, be cured of oxygen vacancies and readjusted in the sensor working point.

Figure 2:
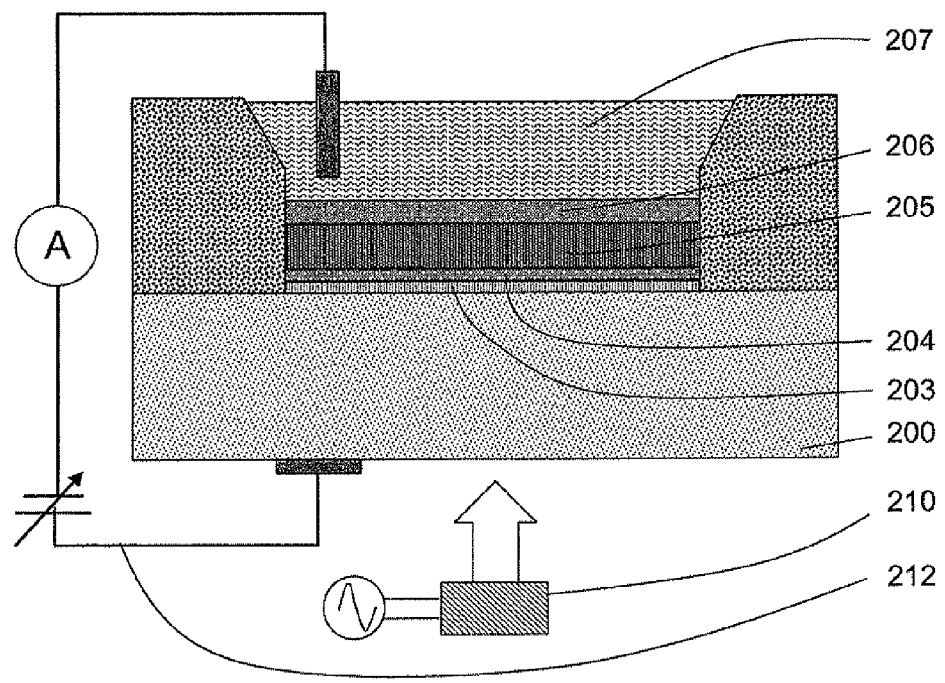
FIG. 2: is a schematic longitudinal section through a LAPS of the invention.

The light-addressable potentiometric sensor (LAPS) shown in FIG. 2 includes a silicon substrate 200, on which a layer sequence 203 to 206 is prepared, which includes a substrate oxide 203, an adapting or matching layer 204, an intermediate insulator 205, and a sensor layer 206. As regards the chemical, structural and morphological properties of the layer sequence of the LAPS of the invention, the explanations for the layers of the same name of the ISFET sensor of the invention hold correspondingly.

The LAPS of the invention further includes a modulatable (laser) light source 210 for generating photoelectrons in the silicon substrate. The modulated photocurrent which is registered with a measurement circuit 212 and which exists between a measured medium 207, with which the sensor layer 206 of the LAPS is supplied, and the silicon substrate 200 is a function of the ion concentration of the measured medium, for example, the pH value.

The invention claimed is:

1. An ion-sensitive sensor with an EIS structure, comprising:
    a semiconductor substrate, on which a layer of a substrate oxide is produced;
    an adapting or matching layer, which is prepared on the substrate oxide;
    a chemically stable intermediate insulator, which is deposited on the adapting or matching layer; and
    a sensor layer, which comprises a tantalum oxide or a tantalum oxynitride, and which is applied on said intermediate insulator, wherein:
    said intermediate insulator comprises hafnium oxide or zirconium oxide or a mixture of zirconium oxide and hafnium oxide; and
    said adapting or matching layer differs in its chemical composition and/or in its structure from said intermediate insulator and from said substrate oxide.

2. The ion-sensitive sensor with an EIS structure as claimed in claim 1, wherein:
    said adapting or matching layer comprises at least one material selected from a group of materials which includes: hafnium oxide silicate, zirconium oxide silicate, mixtures of hafnium oxide-zirconium oxide silicate, hafnium oxynitride silicate, hafnium oxide, zirconium oxynitride silicate, mixtures of hafnium oxynitride-zirconium oxynitride silicate, tantalum oxide, tantalum oxynitride, tantalum hafnium oxynitride, mixtures of tantalum-hafnium oxide silicate, mixtures of tantalum hafnium oxynitride silicate, hafnium lanthanum oxide, hafnium lanthanum oxynitride, hafnium cerium oxide or hafnium cerium oxynitride.

3. The ion-sensitive sensor with an EIS structure as claimed in claim 1, wherein:
    said substrate oxide has a layer thickness of 2.5 nm to 150 nm, especially not less than 10 nm and not more than 50 nm.

4. The ion-sensitive sensor with an EIS structure as claimed in claim 1, wherein:
    a thickness of said adapting or matching layer amounts to 1 nm to 135 nm, especially not less than 5 nm and not more than 35 nm.

5. The ion-sensitive sensor with an EIS structure as claimed in claim 1, wherein:
    said intermediate insulator has a layer thickness of 20 nm to 200 nm, especially not less than 50 nm and not more than 170 nm, preferably not less than 100 nm and not more than 150 nm.

6. The ion-sensitive sensor with an EIS structure as claimed in claim 1, wherein:
    said sensor layer has a layer thickness of 10 nm to 200 nm, especially not more than 100 nm, and preferably not more than 50 nm.

7. The ion-sensitive field effect transistor as claimed in claim 1, wherein:
    said adapting or matching layer between said substrate oxide and said intermediate insulator has a transition from an amorphous structure to a nano-crystalline structure.

8. The ion-sensitive sensor with an EIS structure as claimed in claim 1, wherein:
    said intermediate insulator has a polycrystalline structure, especially a nano-crystalline structure.

9. The ion-sensitive sensor with an EIS structure as claimed in claim 1, wherein:
    said sensor layer has an amorphous, partially crystalline or polycrystalline structure, especially a nano-crystalline structure.

* * * * *